United States Patent
Qiu

(10) Patent No.: US 9,199,929 B2
(45) Date of Patent: *Dec. 1, 2015

(54) ALLYL ETHER-TERMINATED FLUOROALKANESULFINIC ACIDS, SALTS THEREOF, AND A METHOD OF MAKING THE SAME

(75) Inventor: Zai-Ming Qiu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 92 days.

This patent is subject to a terminal disclaimer.

(21) Appl. No.: 14/118,670

(22) PCT Filed: May 25, 2012

(86) PCT No.: PCT/US2012/039523
§ 371 (c)(1),
(2), (4) Date: Nov. 19, 2013

(87) PCT Pub. No.: WO2012/166578
PCT Pub. Date: Dec. 6, 2012

(65) Prior Publication Data
US 2014/0088322 A1  Mar. 27, 2014

Related U.S. Application Data

(60) Provisional application No. 61/492,885, filed on Jun. 3, 2011.

(51) Int. Cl.
*C07C 313/04* (2006.01)
*C07C 303/22* (2006.01)
*B01J 31/02* (2006.01)

(52) U.S. Cl.
CPC ............ *C07C 313/04* (2013.01); *C07C 303/22* (2013.01); *B01J 31/0239* (2013.01); *B01J 2231/42* (2013.01)

(58) Field of Classification Search
None
See application file for complete search history.

(56) References Cited

U.S. PATENT DOCUMENTS

| | | | |
|---|---|---|---|
| 4,332,665 A * | 6/1982 | Kimoto et al. | 204/296 |
| 5,285,002 A | 2/1994 | Grootaert | |
| 5,623,038 A * | 4/1997 | Greuel et al. | 526/255 |
| 5,639,837 A | 6/1997 | Farnham | |
| 5,750,797 A | 5/1998 | Vitcak | |
| 5,958,822 A | 9/1999 | Beckerbauer | |
| 6,365,693 B1 | 4/2002 | Hung | |
| 6,462,228 B1 | 10/2002 | Dams | |
| 6,624,328 B1 | 9/2003 | Guerra | |

FOREIGN PATENT DOCUMENTS

| | | |
|---|---|---|
| JP | 2006-131588 | 5/2006 |
| WO | 99/48939 * | 9/1999 |
| WO | WO 2012-082454 | 6/2012 |
| WO | WO 2012-082546 | 6/2012 |
| WO | WO 2012-082551 | 6/2012 |
| WO | WO 2012-082695 | 6/2012 |
| WO | WO 2012-082703 | 6/2012 |

OTHER PUBLICATIONS

Guo, et al., "Perfluoro and Polyfluoro Sulfonic Acids: VI. The Syntheses of Some Long Chain Oxaperfluoroalkane Sulfonic Acids", *Acta Chimica. Sinica*, vol. 40, No. 9, pp. 828-834, (1982).
Hu, "The Chemistry of Perfluoroalkanesulfonyl Halide", *Organic Chemistry*, vol. 9, pp. 498-506 (1989).
Chen, "Synthesis of a potent .beta.-lactamase inhibitor-1,I-dioxo-6-(2-pyridyl)methylenepenicillanic acid and its reaction with sodium methoxide", Tetrahedron Letters, 1986, vol. 27, No. 30, pp. 3449-3452.
Chen, "New Polyfloruoalkoxysulfonyl Fluorides (I)", Journal of Fluorine Chemistry, 1990, vol. 46, pp. 21-38.
Chen, "New Polyflurooalkoxysulfonyl Fluorides Part III", Journal of Fluorine Chemistry, Jun. 1990, vol. 48, No. 1, pp. 107-122.
Chen, "Novel Methods for Incorporation of Fluorosulfonylpolyfuloroalkoxyl Groups, OCFYCF$_2$SO$_2$F, into Aliphatic or Aromatic Compounds", Journal of Fluorine Chemistry, Jun. 1996, vol. 78, No. 2, pp. 103-107.
Hu, "Reaction of Perfluoroalkanesulfinates with Allyl and Propargyl Halides, A Convenient Synthesis of 3-(Perfluoroalkyl) prop-1-enes and 3-(Perfluoroalkyl) allenes", Journal of Organic Chemistry, Apr. 1991, vol. 56, No. 8, pp. 2801-2804.
Huang, "The reaction of perfluoroalkanesulfinates—The study on perfluoroalkanesulfinates as per flu or oalkylation reagents", Acta Chimica Sinica (English Edition), 1989, vol. 47, No. 2, pp. 190-192.
Huang, "The reaction of perfluoroalkanesulfinates IV. Perfluoroalkyl radical addition to olefins initiated by single electron oxidation of perfluoroalkanesulfinate" Chinese Journal of Chemistry, 1990, No. 4, pp. 362-369.
Huang, "Sulfite radical anion and sodium perfluoroalkane sulfinate initiated addition of perfluoroalkyl iodide on double bond", Acta Chimica Sinica (Chinese Edition), 1988, vol. 46, No. 7, pp. 669-673.
Perfluoro Sulfonic Acid Group, "Perfluoro and Ployfluoro Sulfonic Acids—II. The Prepartion of Some Oxapolyfluoroalkane Sulfonic Acids", Acta Chimica Sinca, Nov. 1979, vol. 37, No. 4, pp. 315-324.
International Search Report for PCT International Application No. PCT/US2012/039523 Mailed on Dec. 26, 2012, 4 pages.

* cited by examiner

*Primary Examiner* — Karl J Puttlitz
(74) *Attorney, Agent, or Firm* — Julie Lapos-Kuchar

(57) ABSTRACT

Described herein are allyl ether-terminated fluoroalkylsulfinic acids and salts thereof and methods of making.

5 Claims, No Drawings

ALLYL ETHER-TERMINATED FLUOROALKANESULFINIC ACIDS, SALTS THEREOF, AND A METHOD OF MAKING THE SAME

CROSS REFERENCE TO RELATED APPLICATIONS

This application is a national stage filing under 35 U.S.C. 371 of PCT/US2012/039523, filed May 25, 2012, which claims priority to U.S. Provisional Application No. 61/492,885, filed Jun. 3, 2011, the disclosure of which is incorporated by reference in its/their entirety herein.

TECHNICAL FIELD

The present disclosure relates to methods of making fluorinated sulfinic acids and salts thereof.

SUMMARY

There is a desire to identify alternative methods for initiating polymerization of fluoromonomers. There is also a need to develop simpler and more cost effective processes for making polymerizable fluorinated sulfinic acid monomers and their corresponding salts. These monomers may be used to co-initiate the polymerization of fluoromonomer(s), which may enable the ability to change the molecular weight or architecture (e.g., linear or branched) and/or change the terminal end-group of a polymer. These monomers may also improve the processability of the fluoropolymer (e.g., solubility in solvents and decreased viscosity) and/or may improve the finished properties (e.g. thermostability, durability, and performance) of the polymerized fluoropolymer.

In one aspect, a composition according to Formula I is described, where Formula I is:

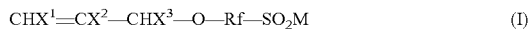

$$CHX^1=CX^2-CHX^3-O-Rf-SO_2M \quad (I)$$

wherein $X^1$, $X^2$, and $X^3$ are each independently selected from the group consisting of: a C1 to C4 alkyl group, an aryl group, H, F, Cl, Br, and I; Rf is a divalent fluorinated group, optionally comprising a catenary oxygen or nitrogen; and M is a cation.

In another aspect, a method is described comprising (a) reacting an allylation compound in the presence of a fluoride salt with a second compound selected from the group consisting of: (i) a fluorinated fluoroacyl sulfonyl fluoride, (ii) a fluorinated sultone to produce an allyl ether-terminated sulfonyl fluoride, and (iii) combinations thereof and (b) reducing the allyl ether-terminated sulfonyl fluoride to produce an allyl ether-terminated fluoroalkanesulfinic acid or salt thereof.

The above summary is not intended to describe each embodiment. The details of one or more embodiments of the invention are also set forth in the description below. Other features, objects, and advantages will be apparent from the description and from the claims.

DETAILED DESCRIPTION

In one application, fluorinated sulfinic acids and their salts have been used to co-initiate the polymerization of fluoromonomers. The fluorinated sulfinic acids and their salts have been used along with oxidizing agents during polymerization of fluoromonomers as described in U.S. Pat. No. 5,285,002 (Grootaert) and U.S. Pat. No. 5,639,837 (Farnham et al.). The fluoropolymers obtained with the fluorinated sulfinate co-initiators have perfluorinated end-groups, which may offer the advantages of better stability and/or improved performance by reducing or eliminating the less stable polar end-groups observed when traditional radical initiators, such as $(NH_4)_2S_2O_8$ are used.

Fluorinated sulfinates having a polymerizable carbon-carbon double bond are of interest for fluoropolymers. Recently carbon-carbon double bond-terminated fluoroalkylsulfinates have been identified as a new class of monomeric initiator, and may be useful as a polymerizable initiator for fluoropolymers as described in U.S. Pat. Publ. No. 2013-0253220. This reference purportedly discloses two methods for making the alkenehalosulfinic acid or salt (or haloalkylsulfinates).

The first method involves reacting a terminal alkene compound with a halofluorosulfonyl fluoride to form a halohydrofluorosulfonyl fluoride, which is dehydrohalogenated and then reduced to produce the haloalkylsulfinates. However, the halofluorosulfonyl fluoride is not readily available and is not cost-effective to make. Further, multiple reaction steps may be necessary to obtain the desired haloalkylsulfinate.

The second method involves reacting a terminal alkene compound with a dihalofluorocarbon to form a haloalkenefluorocarbon halide, which is dehalosulfinated and then dehydrohalogenated to generate a carbon-carbon double bond-terminated haloalkylsulfinate. Traditional synthetic methods require that the reaction of the terminal alkene compound with a dihalofluorocarbon generally has to be controlled at a low conversion in order to achieve high selectivity of the monoaddition product. Further, to control the production of the desired monoaddition, the reaction conditions must be controlled closely, which may be time-consuming.

As used herein, the term

"a", "an", and "the" are used interchangeably and mean one or more;

"and/or" is used to indicate one or both stated cases may occur, for example A and/or B includes, (A and B) and (A or B); and "perfluorinated" as used herein, refers to a perfluorinated carbon group with all C—H bonds being replaced by a C—F bond, that may be linear or branched and embodiments may comprise 2, 3, 4, 6, 8, 10, 12, 18, or even 20 carbon atoms; and "highly-fluorinated" as used herein, refers to a fluorinated carbon group comprising at least 2 fluorine atoms and wherein at least 50%, 60%, 75%, 80%, 90%, 95%, or even 99% of the C—H bonds are replaced by C—F bonds, and the remainder of the carbon bonds are selected from C—H bonds, C—Cl bonds, C—Br bonds, and combinations thereof. The highly-fluorinated group may be linear or branched and embodiments may comprise 2, 3, 4, 6, 8, 10, 12, 18, or even 20 carbon atoms.

Also herein, unless explicitly stated otherwise, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

The present disclosure is directed to an allyl ether-terminated fluoroalkyl sulfinic acid monomer and its method of making. As used herein, "allyl ether-terminated fluoroalkyl sulfinic acid" includes both the acid and a salt thereof, such as for example, the sodium salt form. These allyl ether-terminated fluoroalkyl sulfinic acid monomer compounds may be used in polymerizations.

The monomer of the present disclosure is shown in Formula I:

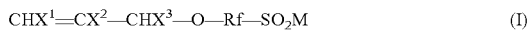

$$CHX^1=CX^2-CHX^3-O-Rf-SO_2M \quad (I)$$

wherein $X^1$, $X^2$, and $X^3$ are each independently selected from the group consisting of: a C1 to C4 alkyl group, an aryl group, H, F, Cl, Br, and I; Rf is a divalent fluorinated group, optionally comprising a catenary oxygen or nitrogen; and M is a cation.

The divalent fluorinated group, Rf, may be perfluorinated or highly-fluorinated. In some embodiments, Rf may be perhalogentated, wherein all of the C—H bonds are replaced with a halogen, such as a fluorine, a chlorine, a bromine atom, or a combination thereof. Rf may or may not comprise double bonds. Rf may be substituted or unsubstituted, linear or branched, cyclic or acyclic, and may optionally comprise a functional group (e.g., ethers, amines, and halides).

In one embodiment, Rf is selected from the group consisting of: $-(CF_2)_a-$, $-(CF_2)_aCFH-$, $-(CF_2)_aCFCl-$, $-(CF_2)_a-O-(CF_2)_b-$, $-[(CF_2CF(CF_3))_a-O]_b-(CF_2)_c-$, $-[(CF_2CF(CF_3))_a-O]_b-(CF_2)_cCFH-$, $-[(CF_2CF(CF_3))_a-O]_b-(CF_2)_cCFCl-$, and combinations thereof, wherein a, b, and c are independently at least 1, 2, 3, 4, 10, or even 15. In one embodiment, a, b, and c are no more than 18 or even 20.

In one embodiment, Rf is a perfluorinated group, optionally comprising heteroatoms, and $X^1$, $X^2$, and $X^3$ are all hydrogen atoms.

The cation, M, in formula I may comprise H$^+$, an inorganic cation including, but not limited to: Na$^+$, Li$^+$, Cs$^+$, Ca$^{+2}$, K$^+$, NH$_4^+$, Mg$^{+2}$, Zn$^{+2}$, and Cu$^{+2}$, and/or an organic cation including, but not limited to N(CH$_3$)$_4^+$, NH$_2$(CH$_3$)$_2^+$, N(CH$_2$CH$_3$)$_4^+$, NH(CH$_2$CH$_3$)$_3^+$, NH(CH$_3$)$_3^+$, and (CH$_3$CH$_2$CH$_2$CH$_2$)$_4$P$^+$.

In one embodiment, the monomer according to formula I includes: $CH_2=CH-CH_2-O-(CF_2)_n-SO_2M$, wherein n is at least 2, 3, 4, 5, 6, 10, or even 20 and M is a cation as defined as above.

In the present disclosure, the monomer according to formula I may be prepared by the method now described.

To prepare the allyl ether-terminated fluoroalkyl sulfinic acid, an allylation compound is reacted in the presence of a fluoride salt with a second compound selected from (i) a fluorinated fluoroacyl sulfonyl fluoride and/or (ii) a fluorinated sultone to produce an allyl ether-terminated sulfonyl fluoride. Then the sulfonyl fluoride with the terminal allyl ether is selectively reduced to produce an allyl ether-terminated fluoroalkyl sulfinic acid.

The first step of the synthesis involves a reaction of (i) a fluorinated fluoroacyl sulfonyl fluoride and/or (ii) a fluorinated sultone with a fluoride salt (QF) to generate a reactive species, [FSO$_2$—Rf'—CF$_2$O$^-$Q$^+$] or [FSO$_2$—CFY—CF$_2$O$^-$Q$^+$], which can then further react with an allylation compound (e.g., (b) below) to produce an allyl ether-terminated sulfonyl fluoride (e.g., (ci) or (cii) below). Such reactions are shown generally with the following schemes:

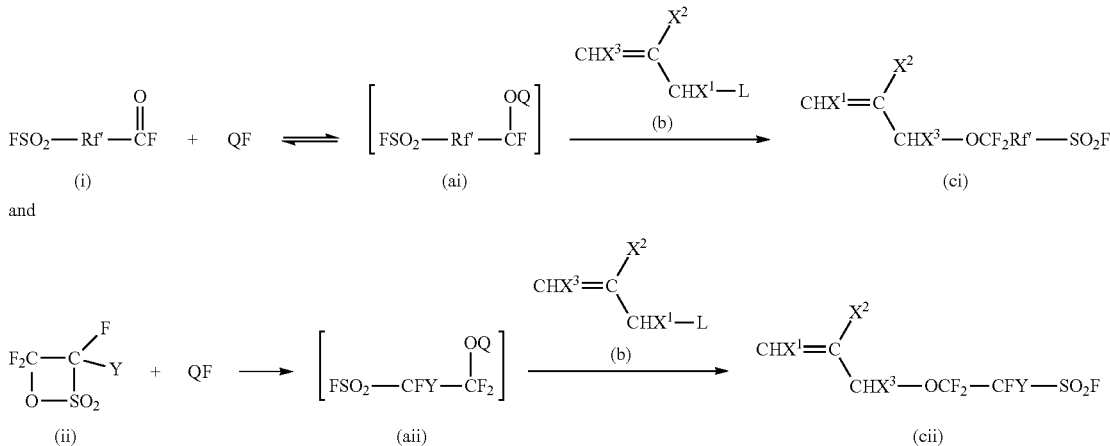

where Rf' is a divalent linking group, Y is a monovalent group, L is a leaving group, and $X^1$, $X^2$, and $X^3$ are defined below.

The allylation compound (e.g., (b) above) as used herein, comprises at least one allyl group substituted with L, a leaving group. The allylation compound may be represented by the formula $CHX^3=CX^2-CHX^1-L$ or $CHX^1=CX^2-CHX^3-L$, wherein $X^1$, $X^2$, and $X^3$ are each independently selected from the group consisting of: H, Cl, F, Br, an aryl group, and an alkyl group (e.g., a short chain alkyl group with C1 to C4 chain), and the leaving group, L, is selected from the group consisting of: I, Br, Cl, F, RC(O)O—, RS(O)$_2$O—, and R$_2$P(O)O—, where each R is independently selected from the group consisting of: an alkyl group, a partially fluorinated alkyl group, and a fully fluorinated alkyl group, which may be linear or branched, cyclic or acyclic, and optionally comprising heteroatoms.

In one embodiment, the allylation compounds used in the present disclosure may include those of the general formula $CH_2=CX^2-CH_2-L$, where $X^2$ is selected from H, Cl, F, Br, an aryl group, and an alkyl group (e.g., a short chain alkyl group with C1 to C4 chain) and L is a leaving group. Exemplary allylation compounds include: $CH_2=CX^2CH_2-L$ where L is selected from Br, I, and Cl, such as $CH_2=CHCH_2Br$; $CH_2=CHCH_2Cl$; $CH_2=CHCH_2I$; $CH_2=CBrCH_2Br$; $CH_2=CClCH_2Cl$; $CH_2=CHCBrF_2$; $CH_2=CBr-CBrF_2$; $CH_2=C(CH_3)CH_2Br$; $CH_2=C(CH_3)CH_2Cl$; $CH_2=C(CH_3)CH_2I$; $CH_2=CHCHBrCH_3$; $CH_2=C(C_6H_5)CH_2Br$; $CH_2=C(C_6H_5)CH_2Cl$; $CH_2=C(C_6H_5)CH_2Cl$; $CH_2=C(C_6H_5)CH_2I$; 1-(1-bromomethyl-vinyl)-4-chloro-benzene; 3-(1-bromomethyl-vinyl)-furan; $CH_2=C(CH_2Br)-CH_2Br$; $CH_2=C(OCH_3)CH_2Br$; $CH_2=C(OCH_2CH_3)-CH_2Br$; 2,3-bis(bromomethyl)-1,3-butadiene; $CH_2=C(CF_3)CH_2Br$. Exemplary allylation compounds include: $CH_2=CX^2CH_2-L$ where L is OC(O)R', such as allyl acetate; allyl 2-furoate; allyl hexanoate; allyl heptanoate; allyl caprylate; allyl nonanoate; allyl cyclohexanebutyrate; dimethallyl carbonate; diallyl succinate; diallyl adipate; allyl butyrate; 2-chloroallyl acetate; and allyl trifluoroacetate. Further examplary allylation compounds include:

$CH_2=CX^2CH_2$-L where L is $-OP(O)R_2$, such as triallyl phosphate and diallyl methylphosphonate. Still further exemplary allylation compounds include: $CH_2=CX^2CH_2$-L where L is $OSO_2R$, such as allyl toluene-4-sulfonate; allyl methanesulfonate; and allyl trifluoromethanesulfonate.

As described above, the allylation compound may be reacted with $[FSO_2-Rf-CF_2O^-Q^+]$ to form the ally ether-terminated fluoroalkyl sulfonyl fluoride. Because, $[FSO_2-Rf-CF_2O^-Q^+]$ is an unstable intermediate, in the present disclosure, it is formed in situ by using either a (i) a fluorinated fluoroacyl sulfonyl fluoride or (ii) a fluorinated sultone in the presence of a fluoride salt.

The fluorinated fluoroacyl sulfonyl fluoride, (i), of the present disclosure is a compound comprising a sulfonyl fluoride, i.e., $(-S(=O)_2F)$ and an fluoroacyl or acyl fluoride group (e.g., $-C(=O)F$). The fluorinated fluoroacyl sulfonyl fluoride may be made using techniques known in the art, including, for example, electrochemical fluorination of a non-fluorinated sultone or carboxylated sulfonyl fluoride in anhydrous HF solution.

In one embodiment, the fluorinated fluoroacyl sulfonyl fluoride may be generated from a sultone as will be described below.

In another embodiment, the fluorinated fluoroacyl sulfonyl fluoride may be generated from the oligomerization of a fluoroacyl sulfonyl fluoride with a fluorinated ethylene oxide, such as hexafluoropropene oxide. An example of such a reaction is shown below.

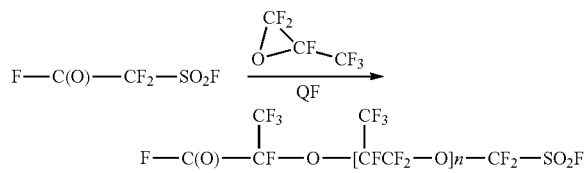

where n is 0 or is at least 1, 2, 4, 10, 20, or even 100.

Exemplary fluorinated fluoroacyl sulfonyl fluorides include: $FC(=O)(CF_2)_3SO_2F$, $FC(=O)(CF_2)_4SO_2F$, $FC(=O)CF(CF_3)O(CF_2)_2SO_2F$, $FC(=O)CF(CF_3)O(CF_2)_3SO_2F$, $FC(=O)CF(CF_3)O(CF_2)_4SO_2F$, $FC(=O)CF(CF_3)OCF_2CF(CF_3)O(CF_2)_2SO_2F$, and $FC(=O)CF(CF_3)OCF_2CF(CF_3)O(CF_2)_4SO_2F$.

The fluorinated sultone, (ii), of the present disclosure is a cyclic sulfonate ester of a hydroxyl sulfonic acid, which comprises at least one fluorine atom. The fluorinated sultone may be perfluorinated or highly-fluorinated. In one embodiment, the fluorinated sultone comprises a halogen atom selected from at least one of Br and Cl. In one embodiment, the fluorinated sultone comprises a four-member ring.

The fluorinated sultone may be made using techniques known in the art, including, for example, the addition of a fluorinated olefin with $SO_3$.

In one embodiment, the fluorinated sultone reacting with a fluoride salt (QF) can form the generally reactive and unstable species, $[Q^{+-}OCF_2-CFY-SO_2F]$, which can react with the allylation compound to form the allyl ether-terminated sulfonyl fluoride, or form a fluorinated fluoroacyl sulfonyl fluoride isomer in the absence of an allylation compound. Such a reaction scheme is generally shown below.

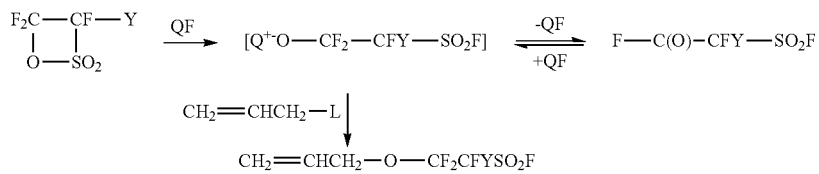

Thus, in one embodiment, the fluorinated fluoroacyl sulfonyl fluoride can be formed from a fluorinated sultone by pre-isomerization or used in situ in the presence of a fluoride anion to react with allylation compound as shown in the reaction scheme above, where QF is a fluoride salt and Y is selected from the group consisting of: F, $CF_3$, Cl, H, and a monovalent perfluorinated or highly-fluorinated group.

Exemplary fluorinated sultones include:

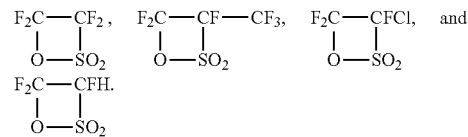

Exemplary fluorinated fluoroacyl sulfonyl fluoride from fluorinated sultones include: $FC(=O)CF_2SO_2F$, $FC(=O)CFClSO_2F$, $FC(=O)CFHSO_2F$, and $FC(=O)CF(CF_3)SO_2F$.

To generate the reactive species, a fluoride salt, QF is used in the presence of a (i) fluorinated fluoroacylsulfonyl fluoride and/or (ii) a fluorinated sultone. Suitable fluoride salts are those which are able to convert the $-COF$ group to $-CF_2OQ$, wherein Q is a cation other than $H^+$, such as sodium, potassium, cesium, or silver. Exemplary fluoride salts include AgF, CsF, NaF, $NH_4F$ and KF.

In one embodiment, the reaction of the allylation compound in the presence of a fluoride salt with the fluorinated fluoroacyl sulfonyl fluoride and/or the fluorinated sultone is performed under anhydrous conditions (i.e., 1000 parts per million (ppm), 100 ppm, 1 ppm, or even no water present). Because water can hydrate the fluoride anion of QF tightly by hydrogen bonding, this can result in significantly reduced fluoride anion reactivity. Therefore, in some embodiments the reaction system is dried before and during the reaction (e.g. in sealed reactor or under dry nitrogen atmosphere), and the level of water in the starting materials and reagents used in the first step of the synthesis is kept low. Preferably, the starting materials and reagents (e.g., solvent or phase transfer catalyst) used in the first step of the synthesis are anhydrous and/or dried prior to use to remove residual water.

In one embodiment, the reaction of the allylation compound with a fluorinated fluoroacyl sulfonyl fluoride or fluorinated sultone may be done in the presence of a phase transfer catalyst increasing the yield by improving the compatibility of the reactants and/or increasing the reactivity of the fluoride anion. Useful phase transfer catalysts for the reaction include for example, quaternary ammonium salts, quaternary phosphonium salts, crown ethers, and polyethylene glycol and derivatives thereof.

Exemplary phase transfer catalyst of quaternary ammonium salts include: $R_4N^{(+)}Z^{(-)}$, where each R is the same or different and comprises an alkyl group being a C1 to C25 chain and Z is an anion, such as $(CH_3CH_2)_4NCl$, $(propyl)_4NCl$, $(butyl)_4NCl$, $(butyl)_4NBr$, $(butyl)_4PBr$, $C_{16}H_{33}N^{(+)}(butyl)_3Br^{(-)}$, $(butyl)_4N^{(+)}CH_3SO_3^{(-)}$, $(butyl)_4N^{(+)}CF_3SO_3^{(-)}$ $(butyl)_4NBr$, and methyltrialkyl ($C_8$-$C_{10}$)ammonium chloride available under the trade designation "ADOGEN 464" produced by Sherex Chemical Co., Mapleton, Ill. As used herein, "propyl" refers to a propyl group and includes both n- and iso-propyl groups. As used herein, "butyl" refers to a butyl group and includes both n-, sec-, iso- and tert-butyl groups.

Exemplary phase transfer catalyst of quaternary phosphonium salts include: $R_4P^{(+)}Z^{(-)}$, where R is same or different alkyl group with C1 to C25 chain and Z is an anion, such as $(CH_3CH_2)_4PCl$, $(C_4H_9)_4PCl$, $(prop)_4PBr$, and hexadecyltrimethylphosphonium bromide.

In one embodiment the reaction of the allylation compound with a (i) fluorinated fluoroacyl sulfonyl fluoride and/or (ii) a fluorinated sultone may be conducted at a temperature of between at least 10, 20, 23, 25, 30, or even 35° C.; at most 70, 80, 90, 100, 150, 200, or even 220° C.

In one embodiment, the reaction between an allylation compound with a (i) fluorinated fluoroacyl sulfonyl fluoride or (ii) a fluorinated sultone is conducted in the presence of a first solvent. Generally, the first solvents have some solubility for the fluoride salt, the allylation compound, and fluorinated fluoroacyl sulfonyl fluoride or fluorinated sultone. The first solvent may be selected from at least one of a polar aprotic solvent and an ether or an alkylated polyether solvent. Exemplary first solvents include polar aprotic solvent selected from N,N-dimethylformamide, dimethyl sulfoxide $CH_3CN$, and other aprotic solvents such as ether or alkylated polyether solvents including tetrahydrofuran, diethyl ether, methyl t-butyl ether, $CH_3OCH_2CH_2OCH_3$, $CH_3OCH_2CH_2OCH_2CH_2OCH_3$, $CH_3O(CH_2CH_2O)_3CH_3$, $CH_3O(CH_2CH_2O)_4CH_3$, and combinations thereof.

The ratio of the allylation compound to the fluorinated fluoroacyl sulfonyl fluoride or the fluorinated sultone is at least 1:1, or even 2:1. Preferably there is an excess of allylation compound.

The second step in the synthesis is a reduction of the allyl ether-terminated sulfonyl fluoride to produce an allyl ether-terminated fluoroalkanesulfinic acid or salt thereof as shown in the equation below:

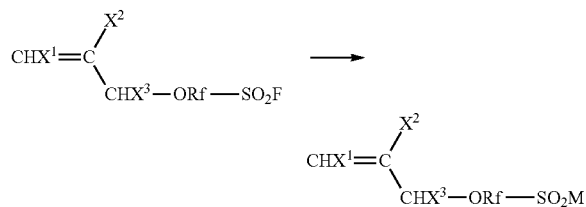

where M is a cation, which may comprise $H^{(+)}$, an inorganic cation, and/or an organic cation.

In some embodiments, the selected reducing agents are highly selective in converting the fluorinated sulfonyl fluoride to the corresponding sulfinate, but not reacting with the terminal allyl group. In other words, the reducing agent and conditions are selected such that the sulfonyl fluoride portion of the molecule is reduced to a sulfinate with substantially no reaction (i.e., less than 10%, 5%, 1% or even 0.5% by mole ratio) with the double bond of the terminal allyl ether and preferably no reaction with the double bond of the terminal allyl ether.

The reducing step may be done in the presence of a reducing agent and a second solvent. The selection of the second solvent may depend on the reducing agent used. Exemplary second solvents include polar aprotic solvents such as, $CH_3CN$, dimethylformamide, dimethyl sulfoxide, and other solvents such as dialkyl ethers (e.g., diethyl ether), t-butyl methyl ether, glycol dialkyl ether (e.g., $CH_3OCH_2CH_2OCH_3$), dioxane, and tetrahydrofuran) and combinations thereof. Exemplary second solvents also include polar protic solvents such as alcohols (e.g., ethanol and isopropanol), acids (e.g. acetic acid) and water, and combinations thereof.

Hydride reducing agents useful in the present disclosure include those represented by the formula, $M'Y'H_4$, wherein M' is an alkali metal or an alkaline Earth metal and Y' is Aluminum or Boron, including, for example, sodium borohydride, sodium cyanoborohydride, potassium borohydride, lithium borohydride, and lithium aluminum hydride. Useful hydride reducing agents also include those represented by the formula, $M''H_n$, wherein M'' is an alkali metal, and n is an integer selected from 1 or 2, including, for example, sodium hydride, lithium hydride, potassium hydride, barium hydride, and calcium hydride. Other useful hydride reducing agents include mono-, di-, or tri(lower alkoxy) alkali metal aluminum hydrides, mono-, di-, or tri-(lower alkoxy lower alkoxy) alkali metal aluminum hydrides, di(lower alkyl) aluminum hydrides, alkalimetalcyanoborohydrides, tri(loweralkyl)tin hydrides, tri(aryl)tin hydrides, $Li(C_2H_5)_3BH$, and $(((CH_3)_2CHCH_2)_2AlH)_2$. Another useful reducing agent for converting—sulfonyl fluoride to sulfinate ($—CF_2SO_2F$ or $—CF_2SO_2M$, where M is a cation as described above, including $H^+$) is sulfites. Useful sulfites include, for example, $K_2SO_3$, $Na_2SO_3$, $KHSO_3$ and $NaHSO_3$. Another useful reducing agent is $NH_2NH_2$.

The monomer according to formula I may be isolated and purified by known methods. In one embodiment, the crude product is isolated from the reaction mixture by filtration to remove insoluble inorganic salts, then rotary evaporation to remove solvent to give a sulfinate solid. In another embodiment, the crude solid is further purified by extracting with solvent, such as isopropanol to remove insoluble inorganic impurity followed by the stripping out of solvent. In another embodiment, the formed sulfinate can be acidified with a strong acid, such as, for example, by addition of sulfuric acid solution to protonate the sulfinate salt resulting to sulfinic acid. In another embodiment, the crude product is isolated by the addition of an acid, such as, for example, sulfuric acid, followed by extraction with an organic solvent, such as t-butyl methyl ether and diethyl ether. The desired product in acid form then is isolated by removal of the organic solvent.

In some embodiments further purification of the crude product is sometimes not necessary. The elimination of the purification step may reduce processing time and cost. If desired, the reaction mixture or crude product may be purified, for example, by repeated recrystallization of the sulfinate salt.

The monomer according to formula I may be useful as a surfactant (emulsifier), a dispersion stabilizer, or an initiator.

Advantageously, the monomer according to formula I may be useful as an initiator for polymers having fewer undesired end-polar groups, or as a polymerizable surfactant, thus eliminating the need to remove the surfactant post-polymerization.

The monomer of the present disclosure, may be used in polymerizations of polymers. Because one end of the monomer according to formula I comprises a double bond, the monomer may be used in polymerization reactions. Because the other end of the monomer according to formula I comprises a sulfinic acid or salt thereof, this site readily forms a radical by electron transfer to an oxidizing agent to generate a radical intermediate which can undergo $SO_2$-elimination. Thus, it may act as an initiator in radical polymerization reaction. Therefore, the monomer according to formula I may be consumed during a polymerization. Furthermore, because of the fast reaction of sulfinic acid and its salt with an oxidizing agent, such as $(NH_4)_2S_2O_8$ to form a fluorinated radical, polymers made using the monomer according to formula I as an initiator may have reduced or no polar end-group generated from the oxidizing agent, which may aid in stability of the polymer.

EXAMPLES

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated.

All materials are commercially available, for example from Sigma-Aldrich Chemical Company; Milwaukee, Wis., or known to those skilled in the art unless otherwise stated or apparent.

These abbreviations are used in the following examples: bp=boiling point, g=gram, mol=mole; ml=milliliter, mm Hg=millimeters of mercury, N=normal, NMR=nuclear magnetic resonance, MW=molecular weight, and ppm=parts per million.

| Materials | |
|---|---|
| Material | Source |
| $FSO_2(CF_2)_3C(O)F$ | Prepared as described in U.S. Pat. No. 6,624,328 (Guerra) |
| t-BuOMe | t-butyl methyl ether, available from EMD Chemicals, Inc., Gibbstown, NJ |
| ADOGEN 464 | methyltri(C8-C10)alkylammonium chloride, commercially available under the trade designation "ADOGEN 464" from Sigma-Aldrich. |

Example 1

160 g dried diglyme, 28 g KF (MW=58.1, 0.48 mol), 11.5 g ADOGEN 464 in 11.5 g diglyme, 100 g $FSO_2(CF_2)_3C(O)F$ (MW=280, 0.35 mol) and 65 g $CH_2$=$CHCH_2Br$ (MW=121, 0.537 mol) were charged under nitrogen into a 600 ml stainless steel reactor with mechanical stirring (commercially available from Parr Instrument Co., Moline, Ill.). The reaction mixture was further reacted at 52° C. for 24 hrs. $^{19}F$ NMR analysis of the reaction mixture showed complete reaction of —C(O)F (+22 ppm, 100% conversion) and the formation of a new —$CF_2O$-signal at −86 ppm. The reaction mixture was filtered to remove solid and the solution was washed with water (3 times with 30 mL each time). The isolated bottom solution was dried over $MgSO_4$ and distilled to yield 78 g (0.23 mol) of a colorless liquid (bp 62° C./14 mmHg). The isolated yield was 65.5%. NMR analysis confirmed the structure $CH_2$=$CHCH_2O(CF_2)_4SO_2F$. $^{19}F$ NMR: +44 (—$SO_2F$, 1F) ppm, −86 (—$OCF_2$—, 2F) ppm, —108 (—$CF_2SO_2F$, 2F) ppm, −121 (—$CF_2$—, 2F) ppm, −126 (—$CF_2$—, 2F) ppm. $^1H$-NMR: 5.9 (m, 1H) ppm, 5.4 (d, 1H) ppm, 5.3 (d, 1H) ppm, 4.6 (d, 2H) ppm.

50 g distilled water, 50 g $CH_3OCH_2CH_2OCH_3$ and 15.64 g $K_2SO_3$ (MW=158.26, 0.988 mol) were charged into a 250 ml three-neck flask, equipped with a magnetic stirrer, a condenser, a nitrogen inlet and a funnel. 18 g $CH_2$=$CHCH_2O(CF_2)_4SO_2F$ (MW=340, 0.053 mol) was added at 20° C. through the funnel and the mixture was reacted for 18 hrs at 20° C. under nitrogen. Analysis of the reaction mixture by $^{19}F$ NMR showed 64% conversion, identified by the reduced signal of —$SO_2F$ at +44 ppm, reduced signal of $CF_2SO_2F$ at −108 ppm and new signal of −$CF_2SO_2K$ at −130 ppm. The mixture was filtered and 8.14 g of a bottom layer was isolated. The bottom layer was recovered $CH_2$=$CHCH_2O(CF_2)_4SO_2F$ as confirmed by $^{19}F$ NMR analysis. $CH_3OCH_2CH_2OCH_3$ was removed by rotary evaporation from the top layer, and the residue was acidified with 2N $H_2SO_4$ and extracted with MeOBu-t (3×60 mL). The combined ether solution was washed with 0.1N $H_2SO_4$ (2 times with 10 mL) and dried over $MgSO_4$. The dried solution was filtered and rotary evaporated to remove the solvent, yielding 7.12 g of the desired product $CH_2$=$CHCH_2O(CF_2)_4SO_2H$ as confirmed by NMR analyses (MW=322, 65% isolated yield). $^{19}F$ NMR: −87 (—$OCF_2$—, 2F) ppm, −125 (—$CF_2$—, 2F) ppm, −128 (—$CF_2$—, 2F) ppm, −130 (−$CF_2SO_2H$, 2F) ppm. $^1H$-NMR: 5.9 ppm (m, 1H), 5.4 ppm (d, 1H), 5.3 ppm (d, 1H), 4.6 (d, 2H) ppm.

Foreseeable modifications and alterations of this invention will be apparent to those skilled in the art without departing from the scope and spirit of this invention. This invention should not be restricted to the embodiments that are set forth in this application for illustrative purposes.

What is claimed is:

1. A monomer comprising a composition according to formula I:

$$CHX^1=CX^2—CHX^3—O—Rf—SO_2M \qquad (I)$$

wherein $X_1$, $X_2$, and $X_3$ are each independently selected from the group consisting of: a C1 to C4 alkyl group, an aryl group, H, Cl, Br, F, and I; Rf is a divalent fluorinated group, optionally comprising a catenary oxygen or nitrogen; and M is a cation.

2. The monomer according to claim 1, wherein $X^1$, $X^2$, and $X^3$ are each independently selected from the group consisting of: a C1 to C4 alkyl group and H.

3. The monomer according to claim 1, wherein Rf is a perfluorinated group.

4. The monomer according to claim 1, wherein the composition is selected from $CH_2$=$CH$—$CH_2$—$O$—$(CF_2)_n$—$SO_2M$, wherein n is at least 2 and M is a cation.

5. The monomer according to claim 1, wherein M is selected from: $H^+$, $Na^+$, $Li^+$, $Cs^+$, $NH_4^+$, and $K^+$.

* * * * *

UNITED STATES PATENT AND TRADEMARK OFFICE
CERTIFICATE OF CORRECTION

| | | |
|---|---|---|
| PATENT NO. | : 9,199,929 B2 | Page 1 of 1 |
| APPLICATION NO. | : 14/118670 | |
| DATED | : December 1, 2015 | |
| INVENTOR(S) | : Qiu | |

It is certified that error appears in the above-identified patent and that said Letters Patent is hereby corrected as shown below:

<u>On the title page</u>
Item 54, and in the specification, column 1, line 1-4 should read "ALLYL ETHER-TERMINATED FLUOROALKYL SULFINIC ACIDS AND SALTS THEREOF".

In the specification

<u>Column 1,</u>
Line 49, delete "thereof" and insert -- thereof; --, therefor.

Signed and Sealed this
Twelfth Day of April, 2016

Michelle K. Lee
*Director of the United States Patent and Trademark Office*